United States Patent
Shaughnessy et al.

(10) Patent No.: US 10,209,205 B2
(45) Date of Patent: Feb. 19, 2019

(54) SYSTEM AND METHOD FOR TIRE INSPECTION

(71) Applicant: Analogic Corporation, Peabody, MA (US)

(72) Inventors: Charles H. Shaughnessy, Hamilton, MA (US); Steven N. Urchuk, Melrose, MA (US); Basak Ulker Karbeyaz, Concord, MA (US)

(73) Assignee: Analogic Corporation, Peabody, MA (US)

( * ) Notice: Subject to any disclaimer, the term of this patent is extended or adjusted under 35 U.S.C. 154(b) by 162 days.

(21) Appl. No.: 15/307,868

(22) PCT Filed: Apr. 29, 2014

(86) PCT No.: PCT/US2014/035850
§ 371 (c)(1),
(2) Date: Oct. 31, 2016

(87) PCT Pub. No.: WO2015/167457
PCT Pub. Date: Nov. 5, 2015

(65) Prior Publication Data
US 2017/0059496 A1    Mar. 2, 2017

(51) Int. Cl.
*G01N 23/18*  (2018.01)
*G01M 17/02*  (2006.01)

(52) U.S. Cl.
CPC ........ *G01N 23/185* (2013.01); *G01M 17/028* (2013.01); *G01N 2223/3304* (2013.01);
(Continued)

(58) Field of Classification Search
None
See application file for complete search history.

(56) References Cited

U.S. PATENT DOCUMENTS

| 7,724,866 B2 | 5/2010 | Naidu et al. |
| 2011/0222754 A1* | 9/2011 | Zhao ................ G06T 7/0004 382/141 |
| 2012/0045033 A1* | 2/2012 | Stuke ............... G01M 17/013 378/62 |

FOREIGN PATENT DOCUMENTS

| CN | 101957329 A | 1/2011 |
| WO | 2014055066 A1 | 4/2014 |

OTHER PUBLICATIONS

International Search Report cited in related application No. PCT/US14/35850 dated Aug. 1, 2014, pp. 11.

(Continued)

*Primary Examiner* — Hoon K Song
(74) *Attorney, Agent, or Firm* — TraskBritt

(57) ABSTRACT

Among other things, a tire inspection system and method are provided. A radiation source and a detector array are configured to rotate about an axis of rotation. During a first examination of a tire, the tire has a first orientation relative to the axis of rotation, and during a second examination, the tire has a second orientation relative to the axis of rotation. For example, between the first examination and the second examination, the tire is at least one of shifted with respect to the axis of rotation or rotated about a tire rotation axis (e.g., perpendicular to the axis of rotation) to change the orientation of the tire relative to the axis of rotation. In this manner, imagery of the tire may be developed, which can be inspected to identify irregularities, etc., in the tire, for example.

23 Claims, 7 Drawing Sheets

(52) U.S. Cl.
CPC . *G01N 2223/627* (2013.01); *G01N 2223/643* (2013.01); *G01N 2223/646* (2013.01)

(56) References Cited

OTHER PUBLICATIONS

Written Opinion of the International Searching Authority for PCT Application No. PCT/US2014/035850 dated Aug. 1, 2014, six pages.
First Chinese Office Action cited in Chinese Application No. 201480078632.8 dated May 27, 2018, 10 Pgs.

\* cited by examiner

SYSTEM AND METHOD FOR TIRE INSPECTION

CROSS-REFERENCE TO RELATED APPLICATIONS

This application is a national phase entry under 35 U.S.C. § 371 of International Patent Application PCT/US2014/035850, filed Apr. 29, 2014, designating the United States of America and published in English as International Patent Publication WO 2015/167457 A1 on Nov. 5, 2015.

TECHNICAL FIELD

The present application relates to the volumetric imaging of tires and/or other objects via radiation. It finds particular application in industrial applications where tires and/or other objects may be inspected for defects in a non-destructive manner. However, it may also find application in medical environments and/or security environments, particularly if a region of interest within an object is offset from a center region of the object.

BACKGROUND

Tires and other objects are often tested to detect defects that may occur during the manufacturing process and/or to verify the quality of the product. For example, tires may be tested to identify possible tread defects, sidewall defects, belt misalignment, bubbles, and/or inclusions.

The testing techniques may be destructive or non-destructive. Destructive techniques refers to techniques where the product is dissected (e.g., and typically scrapped thereafter) to view an internal portion of the product. Non-destructive techniques refer to techniques that allow the product to be inspected without damaging the product. In the tire industry, such non-destructive techniques have included pneumatic balance techniques, mechanical balance techniques, digital projection imaging techniques, and/or machine vision imaging techniques. While these destructive and non-destructive techniques are useful, such techniques are often merely applied to a sample set of products due to, among other things, the length of time it takes to perform the inspection.

BRIEF SUMMARY

Aspects of the present application address the above matters, and others. According to an aspect, a tire inspection system is provided. The tire inspection system comprises a computed tomography (CT) apparatus configured to examine a tire. The CT apparatus comprises a radiation source configured to emit radiation, a detector array configured to detect at least some of the radiation, and a rotating gantry configured to rotate about an axis of rotation. The radiation source and the detector array are mounted to the rotating gantry and define an examination region through which the tire is translated. The tire inspection system also comprises a tire translator configured to translate the tire through the examination region during at least two instances and a tire mover configured to reorient the tire relative to the axis of rotation between a first instance of the at least two instances and a second instance of the at least two instances.

According to another aspect, a method for examining a tire is provided. The method comprises performing a first examination of the tire while maintaining the tire in a first orientation relative to an axis of rotation. The first examination comprising rotating a radiation source and a detector array about the axis of rotation and translating the tire in a first direction. The method also comprises acquiring first image data of the tire responsive to the performing the first examination and changing an orientation of the tire from the first orientation to a second orientation. The method further comprises performing a second examination of the tire while maintaining the tire in the second orientation relative to an axis of rotation. The second examination comprises at least one of translating the tire in the first direction or translating the tire in a second direction. The method also comprises acquiring second image data of the tire responsive to the performing a second examination.

According to another aspect, a computer-readable medium comprising processor-executable instructions that when executed perform operations is provided. The operations comprise performing a first examination of the tire while maintaining the tire in a first orientation relative to an axis of rotation. The first examination comprises rotating a radiation source and a detector array about the axis of rotation such that a relative orientation between the radiation source and the detector array is substantially fixed during the rotating. The first examination also comprises translating the tire in a first direction. The operations also comprise acquiring first image data of the tire responsive to the performing a first examination and changing an orientation of the tire from the first orientation to a second orientation. The operations also comprise performing a second examination of the tire while maintaining the tire in the second orientation relative to an axis of rotation. The second examination comprises at least one of translating the tire in the first direction or translating the tire in a second direction. The operation further comprises acquiring second image data of the tire responsive to the performing a second examination.

Those of ordinary skill in the art will appreciate still other aspects of the present application upon reading and understanding the appended description.

BRIEF DESCRIPTION OF THE DRAWINGS

The application is illustrated by way of example and is not limited by the figures of the accompanying drawings, in which like references generally indicate similar elements and in which.

DETAILED DESCRIPTION

Figure 1:
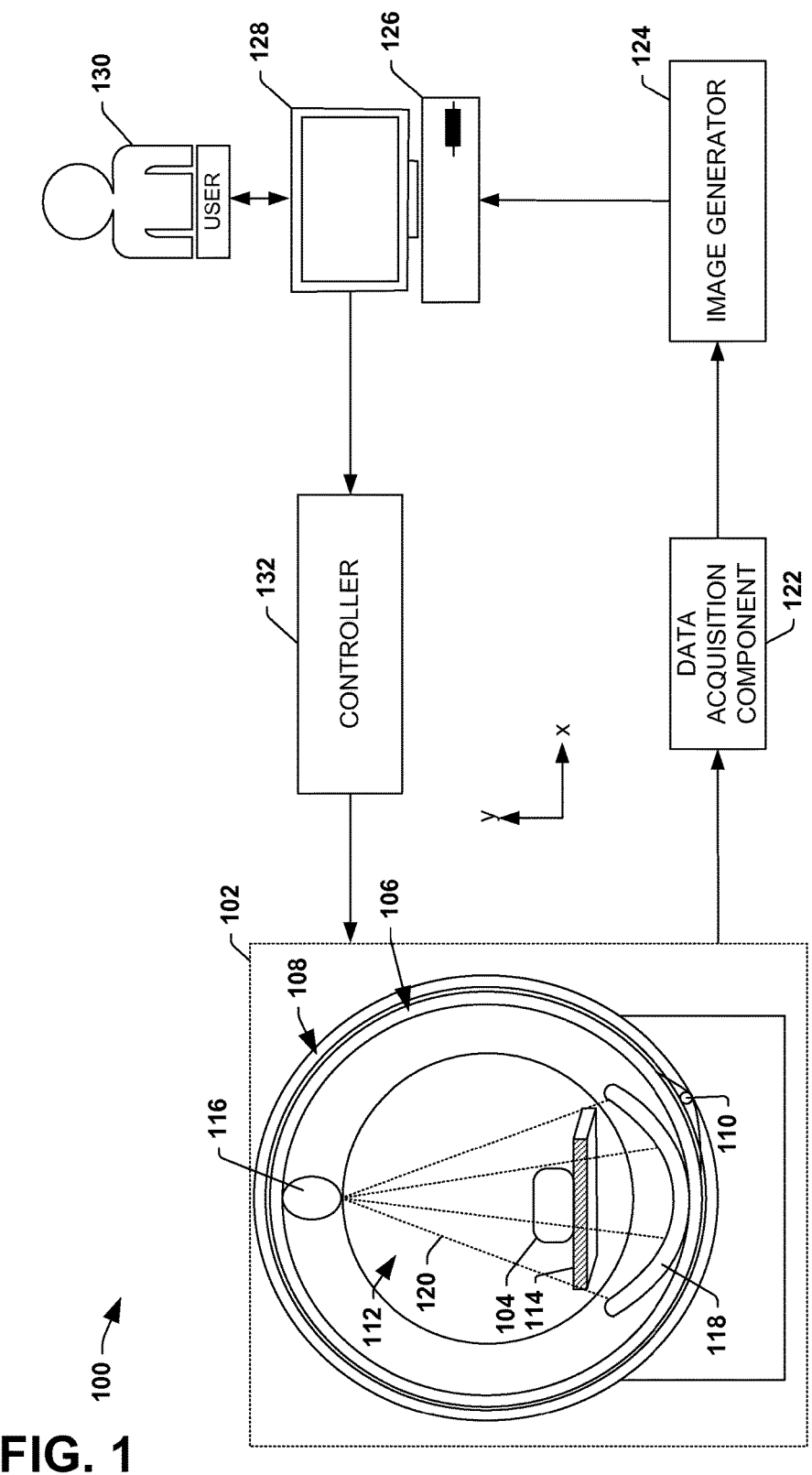
FIG. 1 illustrates an example environment of a tire inspection system.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

Among other things, a tire inspection system configured to generate volumetric data regarding a tire under examination is provided. In some embodiments, the tire is examined via a computed tomography (CT) apparatus configured to examine the tire via radiation from a plurality of angles. In some embodiments, the volumetric data is reconstructed to generate two-dimensional (2D) and/or three-dimensional (3D) images of the tire, which may be inspected by an inspector. In other embodiments, the volumetric data is analyzed by a feature identification component configured to identify specified features, such as defects, within the tire and/or to issue an alert if one or more such features are identified.

In some embodiments, the tire inspection system is configured to be coupled in-stream with a manufacturing conveyance system (e.g., conveyor belt system) and respective tires that are conveyed via the manufacturing conveyance system are inspected by the tire inspection system. Further, in some embodiments, multiple examinations may be performed with respect to the tire, with the orientation being varied between examinations through the tire inspection system. By way of example, between a first examination and a second examination via the tire inspection system, the tire may be rotated to change a rotational position of the tire relative to the tire inspection system. As another example, between the first examination and the second examination, the tire may be shifted (e.g., left or right) such that different portions of the tire are centered within the tire inspection system during respective examinations.

It is to be appreciated that while systems and/or techniques are described herein for inspecting tires, such systems and/or techniques may find applicability to other industrial applications, security applications, and/or medical applications. Accordingly, the instant application is not intended to be limited to merely systems and/or techniques for inspecting tires.

Referring to FIG. 1, an example arrangement of a tire inspection system 100 according to some embodiments is provided. It is to be appreciated that the example arrangement is not intended to be interpreted in a limiting manner, such as necessarily specifying the location, inclusion, and/or relative position of the components depicted therein. By way of example, in some embodiments, the data acquisition component 122 is part of the detector array 118.

An examination unit 102 of the tire inspection system 100 is configured to examine tires 104 to determine one or more characteristics (e.g., attenuation characteristic, density, z-effective, etc.) of an interior portion of respective tires 104. In some embodiments, the examination unit 102 is configured as a CT apparatus and comprises a rotating unit 106 configured to rotate (e.g., within an x, y plane) relative to a stationary unit 108 about an axis of rotation (e.g., extending into and out of the page (e.g., sometimes referred to as the z-direction)) via a rotator 110. By way of example, the rotator 110 may comprise a belt, chain, or gear-system configured to drive the rotating unit 106, causing the rotating unit 106 to be rotated relative to the stationary unit 108. The axis of rotation is generally substantially aligned with an isocenter of the examination unit 102.

The rotating unit 106 comprises a radiation source 116 (e.g., an ionizing radiation source such as an x-ray source or gamma-ray source) and a detector array 118. In some embodiments, the detector array 118 and the radiation source 116 are positioned on substantially diametrically opposing portions of the rotating unit 106, and an examination region 112 is defined between the radiation source 116 and the detector array 118. Tires 104 may be translated through the examination region 112 via a tire translator 114. The tire translator 114 may comprise a conveyer belt assembly, a gravity-fed roller assembly, a mechanical roller assembly, and/or other object translation assembly.

In some embodiments where the radiation source 116 and the detector array 118 are mounted to the rotating unit 106, a relative position between the radiation source 116 and the detector array 118 is substantially maintained during the rotation of the rotating unit 106. In some embodiments, the rotation of the radiation source 116 and detector array 118 (e.g., within an x, y plane) in tandem with the translation of a tire 104 (e.g., in a direction perpendicular to the x, y plane and parallel to the axis of rotation) causes a helical examination to be performed on the tire 104.

As radiation 120 emitted from the radiation source 116 traverses the tire 104, the radiation 120 may be attenuated differently by different aspects of the tire 104. Because different aspects attenuate different percentages of the radiation 120, the number of photons detected by respective detector cells of the detector array 118 may vary. For example, more dense aspects of the tire(s) 104, such as a metal ribbon, may attenuate more of the radiation 120 (e.g., causing fewer radiation photons to impinge a region of the detector array 118 shadowed by the more dense aspects) than less dense aspects, such as air pockets and/or rubber.

Radiation detected by the detector array 118 may be directly or indirectly converted into analog signals that can be transmitted from the detector array 118 to a data acquisition component 122 operably coupled to the detector array 118. The analog signal(s) may carry information indicative of the radiation detected by the detector array 118. The information that can be derived from the analog signal may be a function of whether the detector array 118 is an integrating-type detector array (e.g., configured to integrate charge over a sampling period) and/or a photon counting type detector array (e.g., configured to count detection events and/or determine the energy of respective radiation photons).

The data acquisition component 122 is configured to convert the analog signals output by the detector array 118 into digital signals and/or to compile signals that were transmitted within a predetermined time interval, or measurement interval, using various techniques (e.g., integration, photon counting, etc.). The compiled signals are typically in projection space and are, at times, referred to as projections and/or projection data.

The projections and/or digital signals generated by the data acquisition component 122 may be transmitted to an image generator 124 (e.g., as times referred to as an image reconstructor) configured to convert the data from projection space to image space using suitable analytical, iterative, and/or other reconstruction techniques (e.g., tomosynthesis reconstruction, back-projection, iterative reconstruction, etc.). Such images may depict a 2D representation and/or a 3D representation of the tire 104, for example.

The example CT system also includes a terminal 126, or workstation (e.g., a computer), configured to receive an image(s) from the image generator 124, which can be displayed on a monitor 128 to a user 130 (e.g., a quality inspector). In this way, the user 130 can inspect the image(s) to identify areas of interest (e.g., possible defects) within the tire(s) 104. The terminal 126 can also be configured to receive user input which can direct operations of the examination unit 102 (e.g., a speed of rotation, an energy level of the radiation 120, a desired voltage applied to the radiation source 116, etc.).

In the example tire inspection system 100, a controller 132 is operably coupled to the terminal 126 and may be configured to control operations of the examination unit 102. By way of example, prior to entering the examination region 112, a make, model, and/or other characteristic of the tire 104 (e.g., size characteristic such as diameter) may be received at the terminal 126 from the user 130 and/or from an automated scanning device. Based upon the information provided to the terminal 126, the controller 132 may define a translation speed of the tire translator 114 and/or a rotational speed of the rotating gantry 106. In this way, the controller 132 may define a helical pitch of the examination unit 102 (e.g., and thus the tire inspection system 100) based upon one or more characteristics of the tire 104, for example. As an example, the controller 132 may define a larger helical pitch when a 22-inch diameter tire is being examined than when a 17-inch diameter tire is being examined.

As another example, the controller 132 may adjust a speed at which the tire translator 114 translates the tire 104 based upon a relative position between the tire 104 and the examination region 112 and/or between the tire 104 and the detector array 118. By way of example, the detector array 118 may comprise a sensitive region (e.g., at times referred to as a specified region) and a non-sensitive (e.g., or less sensitive) region. When a first portion of the tire 104 (e.g., such as a treaded portion) is shadowing (e.g., x-ray shadowing) the sensitive region, the controller 132 may be configured to instruct the tire translator 114 to translate the tire 104 at a first speed. When a second portion of the tire 104 (e.g., such as a center cavity) is shadowing the sensitive region, the controller 132 may be configured to instruct the tire translator 114 to translate the tire 104 at a second speed (e.g., a faster speed than the first speed).

As still another example, the controller 132 may be configured to adjust a flux rate of emitted radiation 120 based upon a relative position between the tire 104 and the examination region 112 and/or between the tire 104 and the detector array 118. By way of example, when the first portion of the tire 104 is shadowing the sensitive region of the detector array 118, the controller 132 may be configured to instruct the radiation source 116 to emit radiation 120 at a first flux rate, and when a second portion of the tire 104 is shadowing the sensitive region, the controller 132 may be configured to instruct the radiation source 116 to emit radiation 120 at a second flux rate (e.g., that is less than the first flux rate).

It is to be appreciated the foregoing features are merely example features of a tire inspection system 100 and that other features may be added to the tire inspection system 100 and/or substituted in for one or more of the foregoing features. By way of example, in some embodiments, a feature identification component may be operably coupled to the data acquisition component 122 and/or the image generator 124 and may be configured to receive the projections and/or images. Moreover, such a feature identification component may be configured to analyze the projections and/or images to identify specified features of the tire 104. For example, the feature identification component may be configured to analyze the projections and/or images for possible defects. If a specified feature is identified, the feature identification component may issue an alert to the terminal 126 (e.g., notifying the terminal 126 and/or the user 130 of a possible defect).

As another example, the tire inspection system 100 may comprise a tire diversion component configured to divert tires based upon user input from the user 130 and/or based upon an alert issued by the feature identification component. By way of example, if the user 130 provides an identification that a defect has been identified and/or if the feature identification component identifies a defect in a tire 104, the tire diversion component may divert the tire to a secondary conveyance system (e.g., to be further inspected and/or destroyed).

Figure 2:
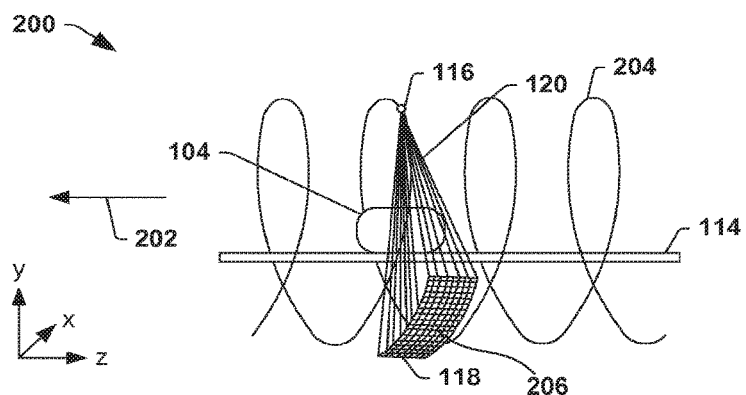
FIG. 2 illustrates a functional diagram of a helical examination performed via an examination unit of a tire inspection system.

Referring to FIG. 2, a functional diagram 200 of a helical examination performed via the examination unit 102 is provided. During an examination of a tire 104, the radiation source 116 and the detector array 118 (e.g., located on substantially opposing sides of the tire translator 114) are rotated about the tire 104 in a plane (e.g., typically defined as an x-y plane) via the rotating gantry 106 while the tire 104 is translated via the tire translator 114 in a direction 202 substantially parallel to the axis of rotation (e.g., such that the tire 104 is translated in the z-direction). In such an environment, the rotation of the radiation source 116 and detector array 118 within an x, y plane in coordination with the translation of the tire 104 in the z-direction, causes the radiation source 116 and the detector array 118 to respectively follow a spiral or helical-like trajectory 204 relative to the tire 104.

Figure 3:
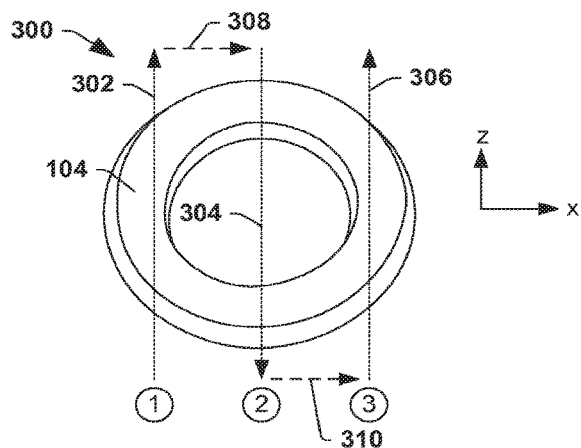
FIG. 3 illustrates an example scan path performed via a tire inspection system.
Figure 4:
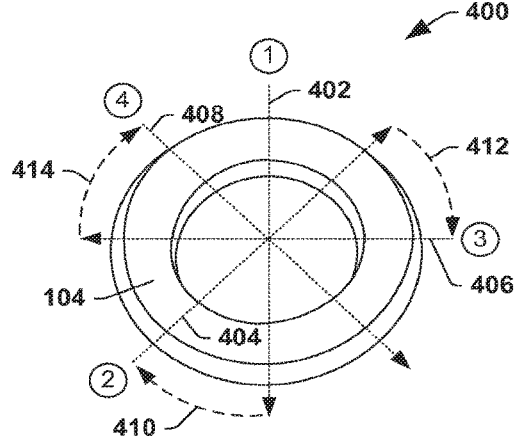
FIG. 4 illustrates an example scan path performed via a tire inspection system.

To acquire an image(s) having a substantially uniform resolution from the examination of a tire 104, for example, the tire 104 may be undergo a plurality of examinations by the examination unit 102, where an examination may be defined as a single pass through the examination region 112. Between respective examinations, the tire 104 may be reoriented relative to the axis of rotation. FIGS. 3-4 illustrate an examples scan paths of the tire 104 for a plurality of examination. At least a portion of the volumetric data yielded from respective examinations (e.g., such as a portion of the volumetric data yielded from a center region of the detector array 118 configured to detect rays of radiation traversing a path spatially proximate the axis of rotation) may subsequently be combined by the image generator 124, for example, to generate a volumetric image of the tire 104.

Referring to FIG. 3, a first example scan path 300 for examining the tire 104 is provided. The dotted lines respectively represent the location of the axis of rotation for the rotating unit 106 relative to the tire 104 during respective examinations. For example, during a first examination (e.g., a first instance through the examination region 112), the tire 104 is positioned relative to the rotating unit 106 such that an axis of rotation is left-of-center relative to the tire 104 (e.g., as indicated by the first dotted line 302). During a second examination (e.g., a second instance through the examination region 112), the tire 104 is positioned relative to the rotating unit 106 such that the axis of rotation is substantially centered on the tire 104 (e.g., as indicated by the second dotted line 304). During a third examination (e.g., a third instance through the examination region 112), the tire 104 is positioned relative to the rotating unit 106 such that the axis of rotation is right-of-center relative to the tire 104 (e.g., as indicated by the third dotted line 306). Between the first examination and the second examination, the tire 104 is shifted in a direction (e.g., x-direction) substantially perpendicular to the axis of rotation (e.g., which extends in the z-direction), as indicated by a first dashed arrow 308. Moreover, between the second examination and the third examination, the tire 104 is again shifted in the direction substantially perpendicular to the axis of rotation, as indicated by a second dashed arrow 310.

As will be described in more detail below, the tire 104 may be translated in different directions during the various examinations. By way of example, during the first examination, the tire 104 may be translated in a first direction as indicated by the arrow of the first dotted line 302 and during the second examination, the tire 104 may be translated in a second direction (e.g., substantially opposite the first direction) as indicated by the arrow of the second dotted line 304). In still other embodiments, respective examinations may be performed by translating the tire 104 in a substantially same direction.

Referring to FIG. 4, a second example scan path 400 for examining a tire 104 is provided. The dotted lines respectively represent the location of the axis of rotation for the rotating unit 106 relative to the tire 104 during respective examinations. For example, during a first examination (e.g., a first instance through the examination region 112), the tire 104 has a first orientation relative to the rotating unit 106 such that the axis of rotation passes through a first portion of the tire 104 (e.g., as indicated by a first dotted line 402). During a second examination (e.g., a second instance through the examination region 112), the tire 104 has a second orientation, different than the first orientation, relative to the rotating unit 106 such that the axis of rotation passes through a second portion of the tire 104 (e.g., as indicated by a second dotted line 404). During a third examination (e.g., a third instance through the examination region 112), the tire 104 has a third orientation, different than the first orientation and the second orientation, relative to the rotating unit 106 such that the axis of rotation passes through a third portion of the tire 104 (e.g., as indicated by a third dotted line 406). During a fourth examination (e.g., a fourth instance through the examination region), the tire 104 has a fourth orientation, different than the first orientation, the second orientation, and/or the third orientation, relative to the rotating unit 106 such that the axis of rotation passes through a fourth portion of the tire 104 (e.g., as indicated by a fourth dotted line 408).

Between respective examinations, the tire 104 may be rotated by a specified number of degrees about a tire rotation axis (e.g., extending in the y-direction) substantially perpendicular to the axis of rotation (e.g., which extends in the z-direction). For example, the tire 104 may be rotated a first number of degrees between the first examination and the second examination, as indicated by a first dashed arrow 410. The tire 104 may be rotated again a second number of degrees between the second examination and the third examination, as indicated by a second dashed arrow 412. The tire 104 may be rotated a third number of degrees between the third examination and the fourth examination, as indicated by a third dashed arrow 414.

As described with respect to FIG. 3, the tire 104 may be translated in different directions during the various examinations. By way of example, during the first examination the tire 104 may be translated in a first direction and during the second examination the tire 104 may be translated in a second direction (e.g., substantially opposite the first direction). In still other embodiments, respective examinations may be performed by translating the tire 104 in a substantially same direction.

Referring to FIGS. 5-8, a perspective view of an interior portion of the examination unit 102 configured to provide for scanning the tire 104 according to the first example scan path 300 in FIG. 3 is illustrated. The examination unit 102 comprises the radiation source 116 and the detector array 118. The detector array 118 comprises a plurality of detector cells 502 typically arranged into columns and rows. The number of columns and/or rows may depend upon, among other things, a desired resolution of images yielded from the examination.

The examination region 112 (e.g., represented by the shaded pyramidal shaped feature) is formed between the radiation source 116 and the detector array 118 and extends in a fan-angle direction (e.g., the x-direction) and a cone-angle direction (e.g., the z-direction). At a given point in time, aspects of the tire 104 intersecting the examination region 112 are being examined (e.g., while other aspects of the tire 104 not intersecting the examination region 112 are not being examined).

As described with respect to FIGS. 1 and 2, the radiation source 116 and the detector array 118 are mounted to a rotating gantry 118 configured to rotate about an axis of rotation (e.g., in an x, y plane) while the tire 104 is translated via a tire translator 114 in a direction substantially parallel to the axis of rotation (e.g., the z-direction). To provide for describing a position of the tire 104 relative to the axis of rotation, a line 504 has been drawn in FIGS. 5-8 to illustrate a location of the axis of rotation.

Figure 5:
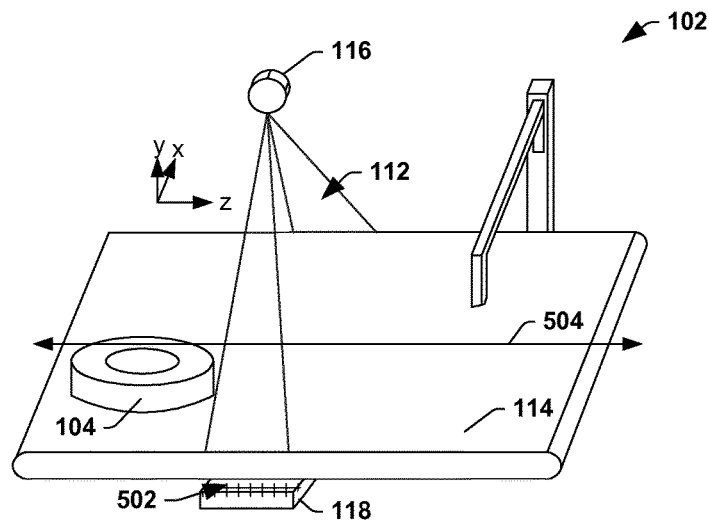
FIG. 5 illustrates a perspective view of an example examination unit.

As illustrated by FIG. 5, when the tire 104 is received by the examination unit 102, the tire 104 may be oriented (e.g., positioned) at a first position relative to the axis of rotation. Such an orientation may be maintained by the tire 104 as the tire 104 is translated through the examination region 112 via the tire translator 114 during a first examination (e.g., a first instance).

Figure 6:
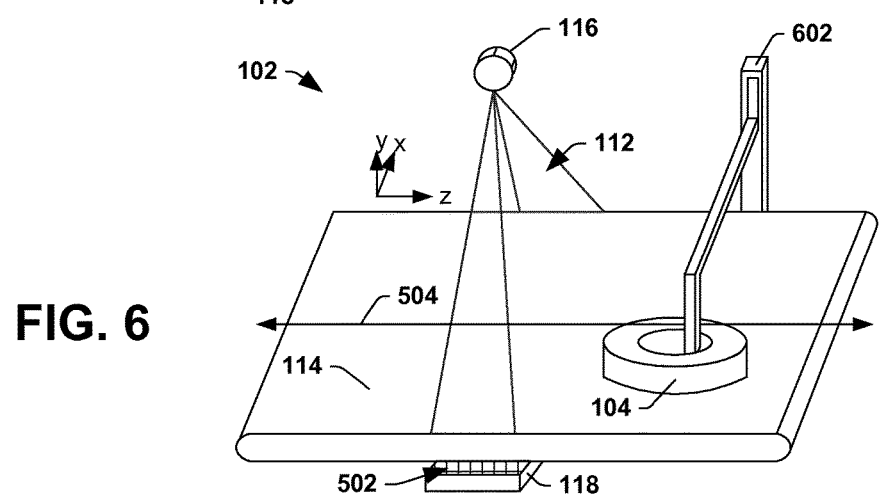
FIG. 6 illustrates a perspective view of an example examination unit.
Figure 7:
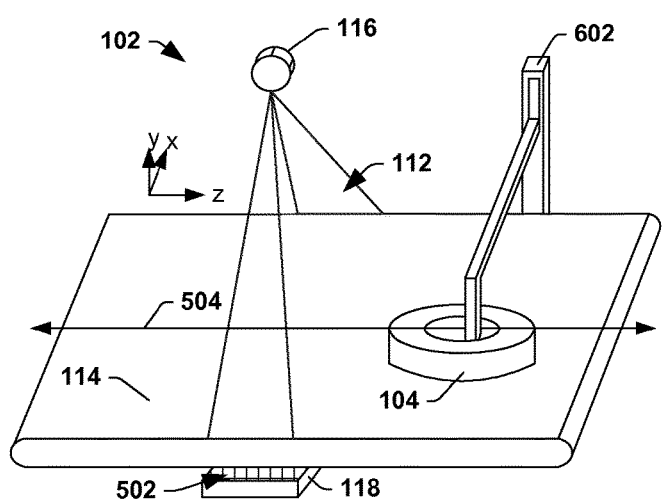
FIG. 7 illustrates a perspective view of an example examination unit.

Turning to FIGS. 6 and 7, upon exiting the examination region 112 after the first examination, a tire mover 602 may contact the tire 104 and reorient the tire 104 relative to the axis of rotation. By way of example, in some embodiments, the tire mover 602 comprises an articulating arm configured to grapple the tire 104, raise the tire 104 off the tire translator 114, reorient the tire 104 relative to the axis of rotation (e.g., centering the tire 104 on the line 504 representative of the axis of rotation as illustrated by FIG. 7), and lower the tire 104 back onto the tire translator 114. In other embodiments, the tire mover 602 may comprise a bar and/or other mechanism that pushes and/or pulls the tire 104 to a desired position relative to the axis of rotation.

Figure 8:
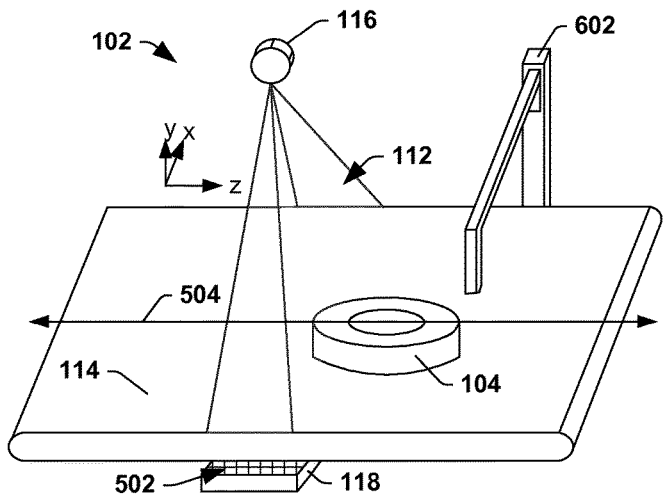
FIG. 8 illustrates a perspective view of an example examination unit.

Turning to FIG. 8, after the tire 104 has been reoriented relative to the axis of rotation, a second examination may be performed on the tire 104 by re-translating the tire 104 through the examination region 112. For example, in some embodiments, the tire translator 114 reverses direction (e.g., relative to a direction of movement during the first examination) to translate the tire 104 back into the examination region 112. Such a process of examining and reorienting the tire 104 may be performed iteratively until a stopping criterion is satisfied (e.g., until the tire 104 has been examined from a specified number of orientations relative to the axis of rotation). In some embodiments, such as where the tire translator 114 does not reverse direction, a second subsequent scanner (e.g., source, detector, etc.) may be downstream to perform the second examination (e.g., the second instance) (e.g., and third, fourth, etc. scanners may be included as well).

Figure 9:
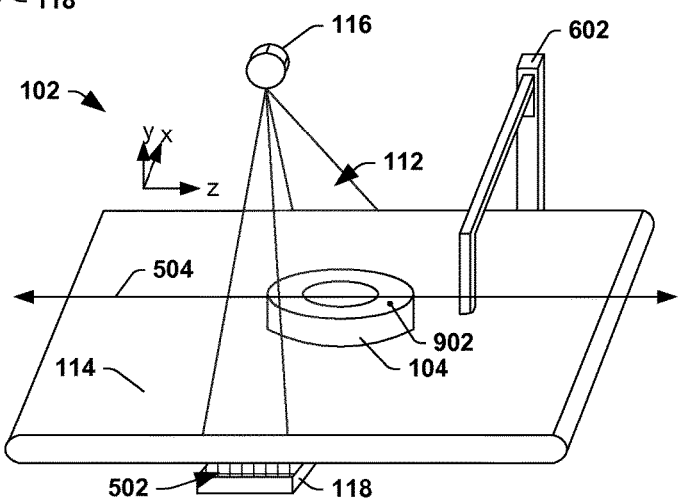
FIG. 9 illustrates a perspective view of an example examination unit.
Figure 10:
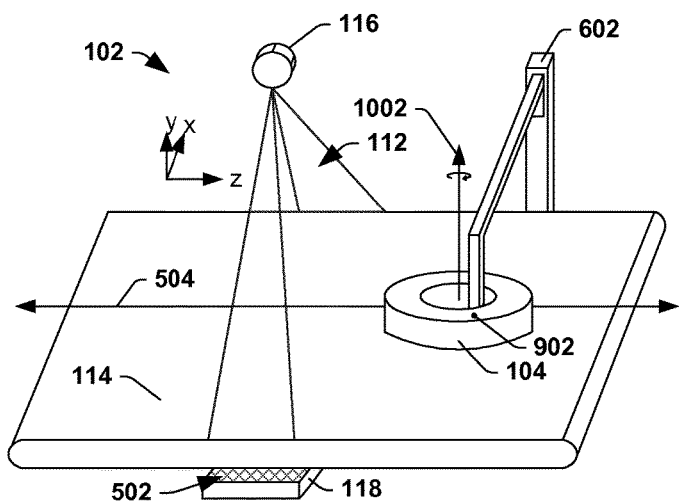
FIG. 10 illustrates a perspective view of an example examination unit.
Figure 11:
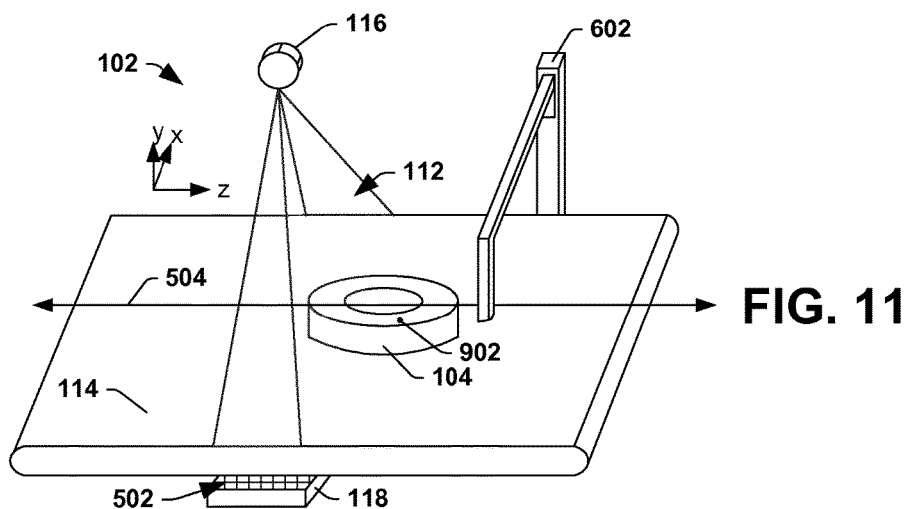
FIG. 11 illustrates a perspective view of an example examination unit.

Referring to FIGS. 9-11, a perspective view of an interior portion of the examination unit 102 configured to provide for scanning the tire 104 according to the second example scan path 400 in FIG. 4 is illustrated. The examination unit 102 comprises the radiation source 116 and the detector array 118. The detector array 118 comprises a plurality of detector cells 502 typically arranged into columns and rows. The number of columns and/or rows may depend upon, among other things, a desired resolution of images yielded from the examination.

The examination region 112 (e.g., represented by the shaded pyramidal shaped feature) is formed between the radiation source 116 and the detector array 118 and extends in a fan-angle direction (e.g., the x-direction) and a cone-angle direction (e.g., the z-direction). At a given point in time, aspects of the tire 104 intersecting the examination region 112 are being examined (e.g., while other aspects of the tire 104 not intersecting the examination region 112 are not being examined).

As described with respect to FIGS. 1 and 2, the radiation source 116 and the detector array 118 are mounted to a rotating gantry 106 configured to rotate about an axis of rotation (e.g., in an x, y plane) while the tire 104 is translated via a tire translator 114 in a direction substantially parallel to the axis of rotation (e.g., the z-direction). To provide for describing an orientation of the tire 104 relative to the axis of rotation, a line 504 has been drawn in FIGS. 9-11 to illustrate a location of the axis of rotation and a black dot 902 has been drawn on the tire 104.

As illustrated by FIG. 9, when the tire 104 is received by the examination unit 102, the tire 104 may be substantially centered on the axis of rotation and may be oriented at a first orientation relative to the axis of rotation. Such an orientation may be maintained by the tire 104 as the tire 104 is translated through the examination region 112 via the tire translator 114 during a first examination (e.g., a first instance).

Turning to FIG. 10, upon exiting the examination region 112 after the first examination, the tire mover 602 may contact the tire 104 and reorient the tire 104 relative to the axis of rotation. By way of example, in some embodiments, the tire mover 602 comprises an articulating arm configured to grapple the tire 104, raise the tire 104 off the tire translator 114, rotate the tire 104 about a tire rotation axis 1002 (e.g., in the y-direction) substantially perpendicular to the axis of rotation (e.g., repositioning the black dot 902 relative to the axis of rotation), and lower the tire 104 back onto the tire translator 114. In other embodiments, other apparatuses for rotating the tire 104 besides and/or in addition to a grapple arm may be used to rotate the tire 104 about the tire rotation axis 1002.

Turning to FIG. 11, after the tire 104 has been reoriented relative to the axis of rotation (e.g., such that the black dot 902 is in a different position relative to the axis of rotation as compared to FIG. 9), a second examination may be performed on the tire 104 by re-translating the tire 104 through the examination region 112. For example, in some embodiments, the tire translator 114 reverses direction (e.g., relative to a direction of movement during the first examination) to translate the tire 104 back into the examination region 112. Such a process of examining and reorienting the tire 104 may be performed iteratively until a stopping criterion is satisfied (e.g., until the tire 104 has been examined from a specified number of orientations relative to the axis of rotation). In some embodiments, such as where the tire translator 114 does not reverse direction, a second subsequent scanner (e.g., source, detector, etc.) may be downstream to perform the second examination (e.g., the second instance) (e.g., and third, fourth, etc. scanners may be included as well).

It may be appreciated that while FIGS. 5-11 illustrate the tire 104 as lying substantially flat on the tire translator 114 (e.g., such that a plane in which a top surface of the tire 104 lays is substantially parallel to a plane of the tire translator 114), in other embodiments, the tire 104 may be inclined relative to a plane of the tire translator 114. For example, a substantially radiation transparent, wedge-shaped object may be inserted between the tire translator 114 and the tire 104 so as to cause the top surface of the tire 104 to not lay in a plane parallel to the plane of the tire translator 114 (e.g., and/or to cause a leading edge of the tire 104 to be raised or lowered relative to a trailing edge of the tire 104). In this way, radiation paths (e.g., between the radiation source 116 and the detector array 118) across a diameter of the tire 104 (e.g., across a width of a tread through metal belts) may be mitigated to reduce potential image artifacts, for example.

Moreover, while the text accompanying FIGS. 3-11 describe the orientation of the tire 104 as being substantially fixed relative to the axis of rotation during an examination (e.g., during respective instances through the examination region 112), in some embodiments, the orientation of the tire 104 may change during an examination. For example, the tire 104 may be rotated intermittently and/or substantially continuously (e.g., by the tire mover 602) during an examination so that angularly spaced image splices may be obtained from the examination. Moreover, as another example, the tire 104 may be positioned in an upright position (e.g., where the axis of rotation for the tire 104 extends in the x-direction and/or z-direction as opposed to in the y-direction as illustrated by FIGS. 5-11) and rolled through the examination unit 102 with or without an applied load and/or pressurization to the tire 104.

Moreover, while FIGS. 5-11 illustrate merely a single tire 104 being examined concurrently, in some embodiments, multiple tires may be examined concurrently, such as by placing the tires in a row (e.g., extending in the x-direction) and/or by stacking the tires (e.g., in the y-direction), for example.

In some embodiments, when an image or images are generated from a scan in which the tire 104 is examined multiple times (e.g., such as described with respect to the scan paths 300 and 400 of FIGS. 3 and 4), the image generator 124 may utilize projection data yielded from merely a portion of the detector cells 206 that detect rays intersecting the axis of rotation and/or intersecting a region spatially proximate the axis of rotation. Projection data yielded from other detector cells 206 may be discarded and/or may be utilized merely for identifying boundaries of the tire 104, for example. Accordingly, the resolution associated with the portion of detector cells that detect rays intersecting the axis of rotation and/or intersecting the region spatially proximate the axis of rotation may be different (e.g., higher) than the resolution associated with a portion of the detector cells detecting rays not intersecting the region by varying one or more characteristics of the detector cells such that a first set of detector cells have a first cell characteristic (e.g., first pitch, first detection area, etc.) and a second set of detector cells have a second cell characteristic (e.g., a second pitch, a second detection area, etc.).

Figure 12:
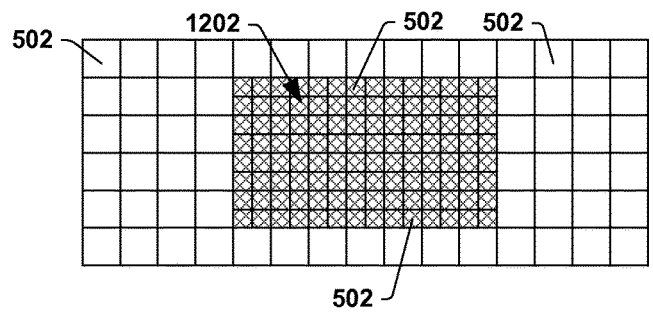
FIG. 12 illustrates a top-down view of an example detector array.
Figure 13:
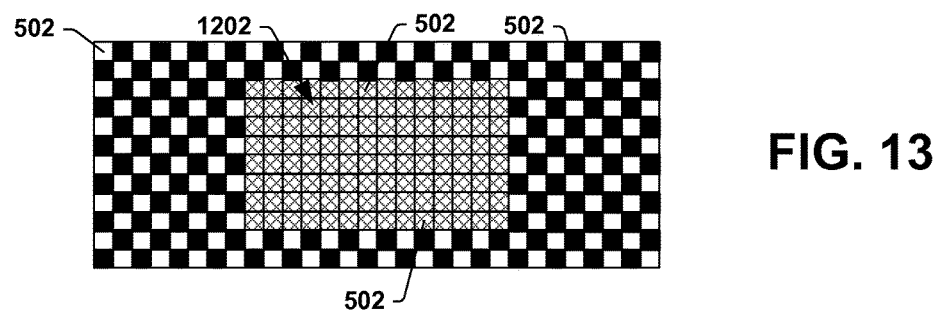
FIG. 13 illustrates a top-down view of an example detector array.

FIGS. 12 and 13 illustrate example detector cells comprising a first set of detector cells having a first cell characteristic and a second set of detector cells having a second cell characteristic. Referring initially to FIG. 12, a top-down view of the detector array 118 (e.g., showing a view of the detector array 118 from the perspective of the radiation source 116) according to some embodiments is provided. In this example, detector cells 502 within a first region 1202 (e.g., a center region defined by the cross-hatching) of the detector array 118 have a smaller surface area (e.g., and thus a higher resolution) than detector cells 502 not within the first region 1202 (e.g., such as detector cells situated proximate a perimeter of the detector array 118). Moreover, in some embodiments, a pitch (e.g., a distance from a center of a first detector cell to a center of a second detector cell) is less for detector cells 502 within the first region 1202 relative to the pitch of detector cells 502 not within the first region 1202.

Referring to FIG. 13, a top-down view of another detector array 118 according to some embodiments is provided. In this example, at least a portion of the detector cells 502 outside of the first region 1202 (e.g., and possibly all detector cells outside of the first region 1202) are inactive (e.g., causing the pitch between two active cells to be greater for detector cells 502 not within the first region). By way of example, the black squares may represent inactive detector cells. It may be appreciated that the example pattern (e.g., a checkerboard pattern) for arranging inactive detector cells is merely one example and that other examples for arranging inactive cells are also contemplated. For example, the inactive detector cells may be arranged into rows and columns (e.g., where an entire row or column of detector cells is inactive). Moreover, in some embodiments, anti-scatter plates may be arranged on top of the detector cells 502 within the first region 1202 while not being arranged on top of at least some detector cells 502 not within the first region 1202.

It may also be appreciated that where at least a portion of the detector array 118 comprises inactive detector cells, a correction (e.g., a truncation correction) may be applied via the data acquisition component 122 and/or the image generator 124, for example. Such a correction may be configured to extrapolate the available projection data (e.g., from the active cells) to estimate the projection data that would have been generated by the inactive cells had the inactive cells been active. In some embodiments, where the shape of the tire 104 being examined is known, simulated projections may be generated and used to estimate the projection data (e.g., to complete the sinogram). For example, the model and/or size of the tire 104 may be scanned prior to and/or during the examination of the tire 104, and simulated projections corresponding to the model and/or size may be retrieved from a database and utilized to estimate the projection data that would have been yielded from inactive detector cells had the inactive detector cells been active.

Figure 14:
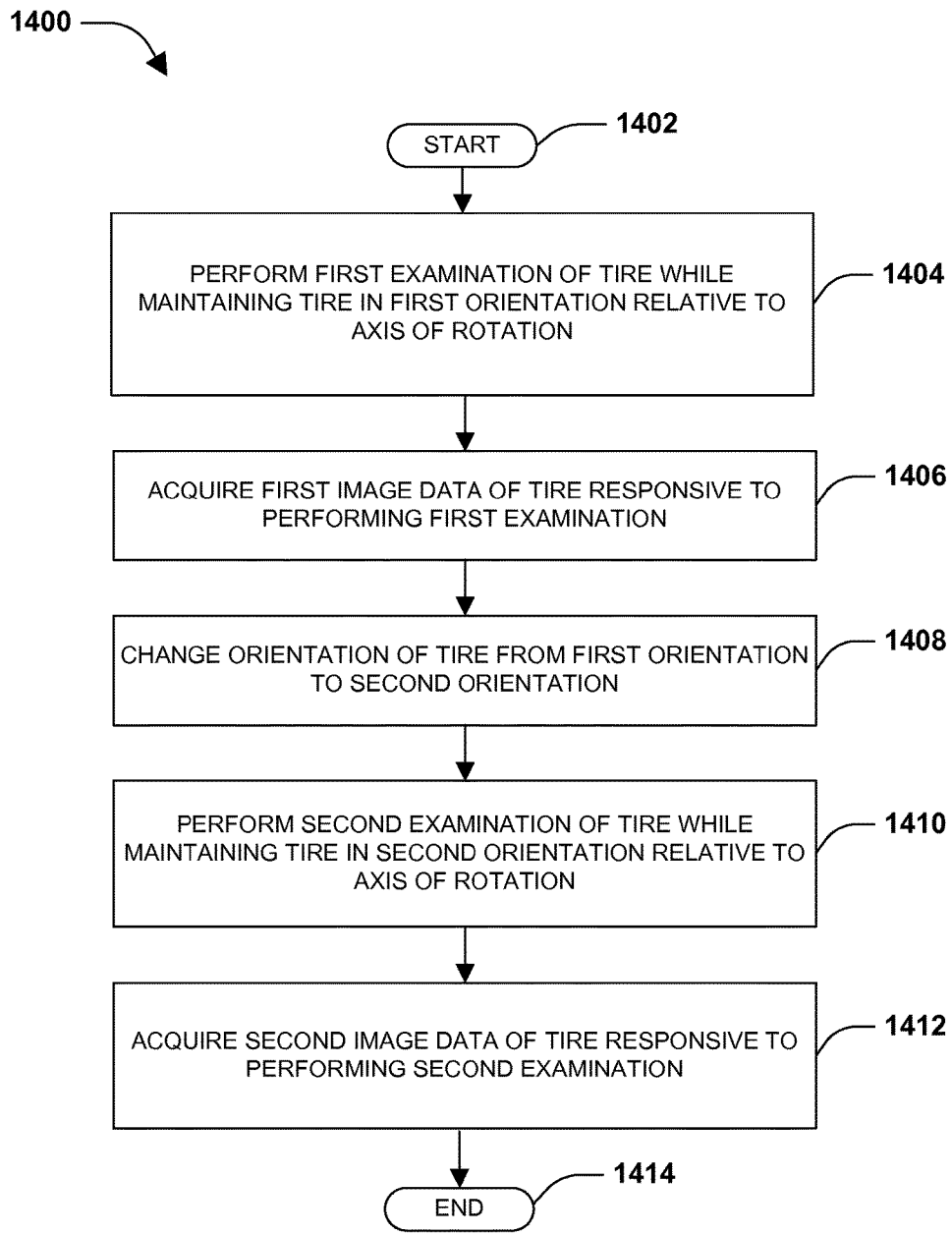
FIG. 14 is a flow diagram illustrating an example method for examining a tire.

Referring to FIG. 14, an example method 1400 for examining a tire is provided. The example method 1400 begins at 1402, and a first examination of the tire is performed while maintaining the tire in a first orientation relative to an axis of rotation of a rotating unit at 1404. During the first examination, the tire is translated in a first direction and a radiation source and a detector array are rotated about the axis of rotation. Typically, a relative orientation between the radiation source and the detector array is substantially fixed during the rotating. At 1406 in the example method, first image data of the tire is acquired responsive to performing the first examination.

At 1408 in the example method 1400, an orientation of the tire is changed from the first orientation to a second orientation. By way of example, the tire may be rotated about a tire rotation axis perpendicular to the axis of rotation to change the orientation of the tire from the first orientation to the second orientation. As another example, the tire may be shifted in a direction perpendicular to the axis of rotation to change the orientation of the tire from the first orientation to the second orientation.

At 1410 in the example method 1400, a second examination of the tire is performed while maintaining the tire in the second orientation relative to the axis of rotation. Generally, during the second examination, the tire is reexamined by the radiation source and the detector array while the tire is translated in at least one of a first direction or a second direction (e.g., opposite the first direction). At 1412 in the example method 1400, second image data of the tire is acquired responsive to performing the second examination.

In some embodiments, at least one of the first image data or the second image data is analyzed, such as by a feature identification component, to identify specified features (e.g., such as specified types of defects). In some embodiments, at least some of the first image data and at least some of the second image data is combined to generate a 2D and/or a 3D image of the tire.

At 1414, the example method 1400 ends.

Figure 15:
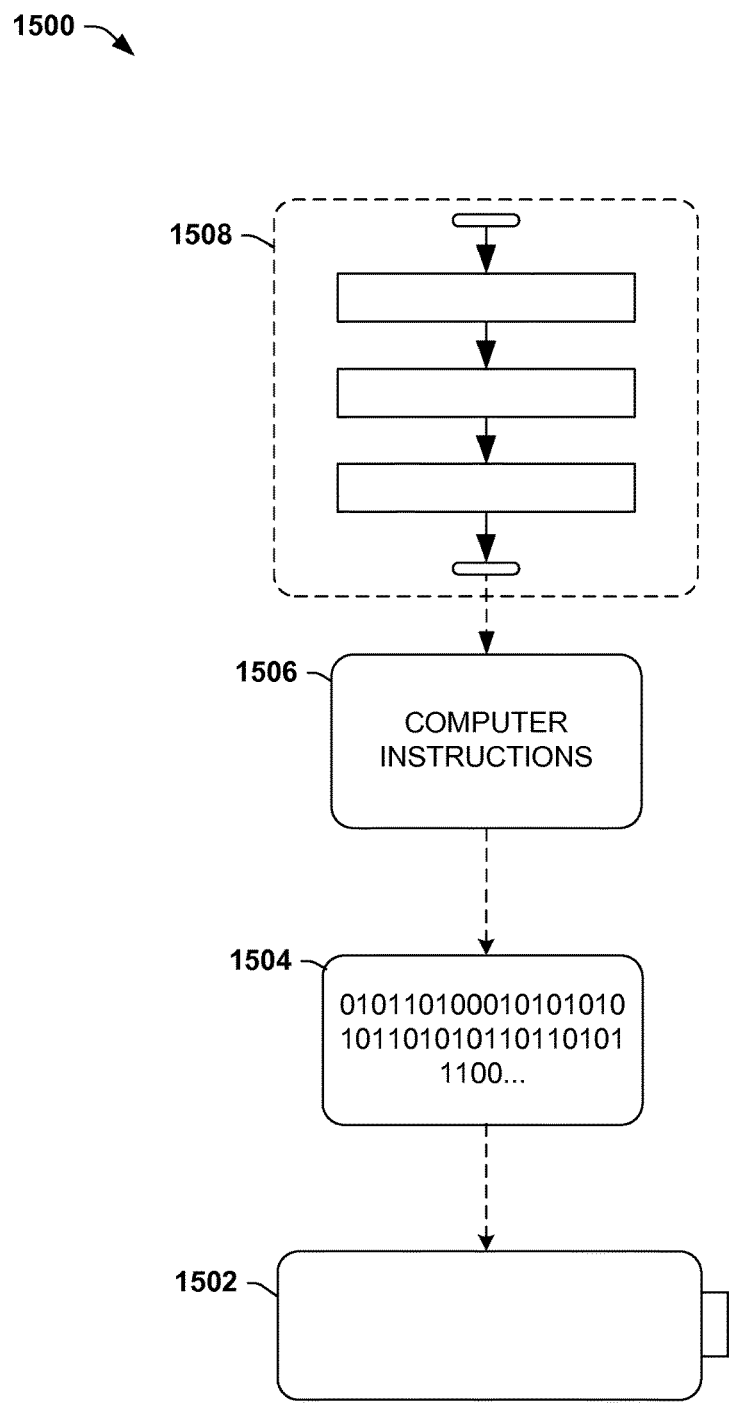
FIG. 15 is an illustration of an example computer-readable medium comprising processor-executable instructions configured to embody one or more of the provisions set forth herein.

Still other embodiments involve a computer-readable medium comprising processor-executable instructions configured to implement one or more of the techniques presented herein. An example computer-readable medium that may be devised in these ways is illustrated in FIG. 15, wherein the implementation 1500 comprises a computer-readable medium 1502 (e.g., a flash drive, CD-R, DVD-R, application-specific integrated circuit (ASIC), field-programmable gate array (FPGA), a platter of a hard disk drive, etc.), on which is encoded computer-readable data 1504. This computer-readable data 1504 in turn comprises a set of processor-executable instructions 1506 configured to operate according to one or more of the principles set forth herein. In some embodiments, the processor-executable instructions 1506 may be configured to perform operations 1508 when executed via a processing unit, such as at least some of the example method 1400 of FIG. 14. In other embodiments, the processor-executable instructions 1506 may be configured to implement a system, such as at least some of the example tire inspection system 100 of FIG. 1. Many such computer-readable media may be devised by those of ordinary skill in the art that are configured to operate in accordance with one or more of the techniques presented herein.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or." In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or two identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A tire inspection system, comprising:
    a computed tomography (CT) apparatus configured to examine a tire, comprising:
        a radiation source configured to emit radiation;
        a detector array configured to detect at least some of the radiation; and
        a rotating gantry configured to rotate about an axis of rotation, the radiation source and the detector array mounted to the rotating gantry and defining an examination region through which the tire translated;
    a tire translator configured to translate the tire through the examination region during at least two instances; and
    a tire mover configured to reorient the tire relative to the axis of rotation between a first instance of the at least two instances and a second instance of the at least two instances;
    wherein the tire inspection system is configured:
        to recognize a feature of the tire responsive to an examination of the tire associated with the first instance, and
        configure at least one of a position, an orientation, a path, or a speed of at least one element of the tire inspection system based on the feature.

2. The tire inspection system of claim 1, wherein the tire mover is configured to reorient the tire by shifting the tire in a direction perpendicular to the axis of rotation.

3. The tire inspection system of claim 1, wherein the tire mover is configured to reorient the tire by rotating the tire about a tire rotation axis perpendicular to the axis of rotation.

4. The tire inspection system of claim 1, wherein the computed tomography apparatus is configured to perform a helical scan of the tire to examine the tire.

5. The tire inspection system of claim 1, wherein the tire translator is configured to translate the tire in a direction parallel to the axis of rotation.

6. The tire inspection system of claim 1, wherein the tire translator is configured to translate the tire in a first direction during the first instance and to translate the tire in a second direction during the second instance, the second direction different than the first direction.

7. The tire inspection system of claim 1, further comprising a controller configured to:
    define a translation speed of the tire translator based upon the feature of the tire; or
    define a rotational speed of the rotating gantry based upon the feature of the tire.

8. The tire inspection system of claim 1, further comprising a controller configured to define a helical pitch of the tire inspection system based upon the feature of the tire.

9. The tire inspection system of claim 1, wherein the detector array comprises:
    a first set of detector cells having a first cell characteristic, and
    a second set of detector cells having a second cell characteristic different than the first cell characteristic.

10. The tire inspection system of claim 9, wherein the first set of detector cells is situated proximate a center of the detector array and the second set of detector cells is situated proximate a perimeter of the detector array.

11. The tire inspection system of claim 1, wherein the operation of the tire translator is configured to translate the tire at a first speed when a feature of a first portion of the tire is recognized shadowing a specified region of the detector array and to translate the tire at a second speed, different than the first speed, when a feature of a second portion of the tire is recognized shadowing the specified region.

12. The tire inspection system of claim 1, wherein the operation of the radiation source is configured to emit the radiation at a first flux rate when a feature of a first portion of the tire is recognized shadowing a specified region of the detector array and to emit the radiation at a second flux rate, different than the first flux rate, when a feature of a second portion of the tire is recognized shadowing the specified region.

13. The tire inspection system of claim 1, further comprising a feature identification component configured to identify a specified feature of the tire based upon image data yielded from the detector array.

14. A method for examining a tire, comprising:
   detecting a feature of a tire and adjusting a position, an orientation, a path, or a speed of a conveyance system based on the characteristic;
   performing a first examination of the tire while maintaining the tire in a first orientation relative to an axis of rotation, the first examination comprising:
      rotating a radiation source and a detector array about the axis of rotation, a relative orientation between the radiation source and the detector array substantially fixed during the rotating; and
      translating the tire in a first direction;
   acquiring first image data of the tire responsive to the performing the first examination;
   changing an orientation of the tire from the first orientation to a second orientation,
   performing a second examination of the tire while maintaining the tire in the second orientation relative to an axis of rotation, the second examination comprising at least one of translating the tire in the first direction or translating the tire in a second direction; and
   acquiring second image data of the tire responsive to the performing a second examination.

15. The method of claim 14, wherein the changing comprises rotating the tire about a tire rotation axis perpendicular to the axis of rotation.

16. The method of claim 14, wherein the changing comprises shifting the tire in a direction perpendicular to the axis of rotation.

17. The method of claim 14, further comprising analyzing at least one of the first image data or the second image data to detect a defect in the tire.

18. The method of claim 14, wherein the first direction is substantially parallel to the axis of rotation.

19. A non-transitory computer-readable medium comprising processor-executable instructions that when executed are configured to enable a computer processor to perform operations, the operations comprising:
   detecting a characteristic of a tire and adjusting a position, an orientation, a path, or a speed of an examination unit based on the characteristic;
   performing a first examination of the tire while maintaining the tire in a first orientation relative to an axis of rotation, the first examination comprising:
      rotating a radiation source and a detector array about the axis of rotation, a relative orientation between the radiation source and the detector array substantially fixed during the rotating; and
      translating the tire in a first direction;
   acquiring first image data of the tire responsive to the performing a first examination;
   changing an orientation of the tire from the first orientation to a second orientation,
   performing a second examination of the tire while maintaining the tire in the second orientation relative to an axis of rotation, the second examination comprising at least one of translating the tire in the first direction or translating the tire in a second direction; and
   acquiring second image data of the tire responsive to the performing a second examination.

20. The non-transitory computer-readable medium of claim 19, wherein the operations comprise combining at least a first portion of the first image data with a second portion of the second image data.

21. The tire inspection system of claim 1, wherein the tire mover is configured to reorient the tire relative to the axis of rotation during a time period at least partially between the first instance and the second instance.

22. The tire inspection system of claim 1, wherein the tire inspection system is configured to modify a position, orientation, path, or speed of at least one of the tire translator or the tire mover based on the characteristic.

23. The tire inspection system of claim 1, wherein the feature of the tire recognized by the tire inspection system comprises at least one of a make, a model, a size, a region, and a relative position of the tire.

* * * * *